US012642790B2

(12) United States Patent
Vieira-Potter et al.

(10) Patent No.: US 12,642,790 B2
(45) Date of Patent: Jun. 2, 2026

(54) DRUG COMBINATION FOR TREATING OBESITY

(71) Applicant: The Curators of the University of Missouri, Columbia, MO (US)

(72) Inventors: Victoria J. Vieira-Potter, Columbia, MO (US); Dennis B. Lubahn, Columbia, MO (US); Eric D. Queathem, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 18/151,232

(22) Filed: Jan. 6, 2023

(65) Prior Publication Data

US 2023/0210826 A1 Jul. 6, 2023

Related U.S. Application Data

(60) Provisional application No. 63/266,491, filed on Jan. 6, 2022.

(51) Int. Cl.
| | |
|---|---|
| *A61K 31/426* | (2006.01) |
| *A61K 31/195* | (2006.01) |
| *A61K 31/36* | (2006.01) |
| *A61P 3/04* | (2006.01) |
| *C07K 16/28* | (2006.01) |

(52) U.S. Cl.
CPC .......... *A61K 31/426* (2013.01); *A61K 31/195* (2013.01); *A61K 31/36* (2013.01); *A61P 3/04* (2018.01); *C07K 16/2863* (2013.01)

(58) Field of Classification Search
CPC ........ A61K 31/426; A61K 31/195; A61P 3/04
See application file for complete search history.

(56) References Cited

U.S. PATENT DOCUMENTS

| | | | |
|---|---|---|---|
| 2007/0043108 A1* | 2/2007 | Lephart ................. | A61K 31/35 |
| | | | 514/456 |
| 2018/0028491 A1* | 2/2018 | Jackson ............. | G01N 33/6896 |
| 2021/0188898 A1* | 6/2021 | Micalizio ............. | C07C 401/00 |

FOREIGN PATENT DOCUMENTS

WO    WO 2006/088716    *   8/2006

OTHER PUBLICATIONS

Compton et. al. (J. Med. Chem. (2004) 47:5872-5893). (Year: 2004).*
Perrone et. al. (Expert Opin. Ther. Patents (2011) 21:505-536). (Year: 2011).*
Sasayama et. al. (Scientific Reports (Jul. 2017) 7:1-8) (Year: 2017).*
Queathem et. al. (FASEB Journal (Apr. 2020) vol. 34 S1, Biology 2020 Meeting Abstracts) (Year: 2020).*
Queathem et. al. (FASEB Journal (Apr. 2020) vol. 34 S1, Biology 2020 Meeting Abstract) (Year: 2020).*

* cited by examiner

*Primary Examiner* — Marcos L Sznaidman
(74) *Attorney, Agent, or Firm* — Tracey S. Truitt; Sandberg Phoenix & von Gontard PC

(57) ABSTRACT

The present invention provides methods of treating obesity, pre-diabetes, diabetes, and/or obese breast cancer, by increasing mitochondrial metabolism by increasing activity of uncoupling protein 1 (UCP1) in adipocytes. The disclosed methods comprise contacting an adrenergic receptor agonist with an adipocyte in which the genomic activity of estrogen receptor beta (ERβ) has been inhibited or inactivated. In certain aspects, inhibition or inactivation of the genomic activity of ERβ is achieved by contacting the adipocyte with an ERβ ligand that selectively inhibits or inactivates the ERβ genomic activity.

5 Claims, 4 Drawing Sheets

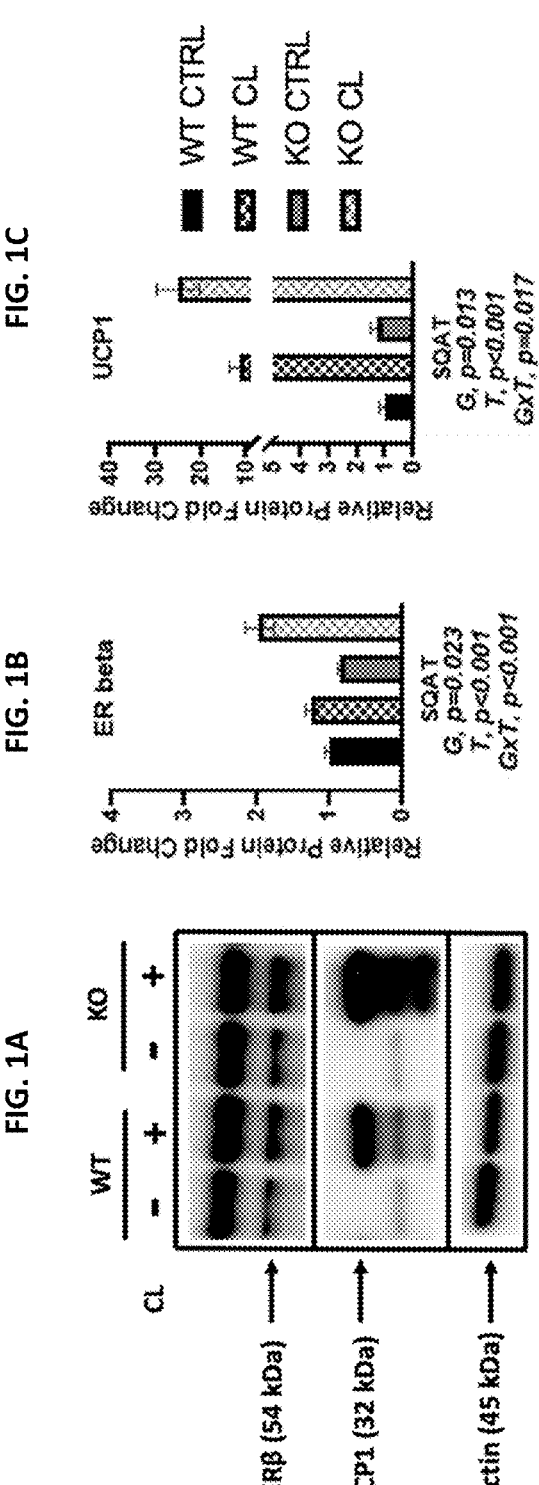

DRUG COMBINATION FOR TREATING OBESITY

RELATED APPLICATIONS

This application relates to and claims priority to U.S. Provisional Patent Application No. 63/266,491, filed on Jan. 6, 2022, the teachings and contents of which are hereby incorporated by reference in their entireties.

BACKGROUND

Obesity, which is currently defined as having a body mass index (BMI) of greater than 30, has become a major health concern, not only in the Western societies, but around the globe. There is strong evidence of genetic predisposition to fat accumulation, and obesity tends to run in families. However, the rise in obesity in populations worldwide in the last four decades has outpaced the rate at which genetic mutations are normally incorporated into populations on a large scale. Moreover, there is a growing number of obese persons in parts of the world where obesity was once rare. According to the World Health Organization (WHO), which considered global obesity an epidemic, in 2016 more than 1.9 billion adults (age 18 or older) worldwide were over-weight and 650 million, representing 13 percent of the world's adult population, were obese.

While obesity is often viewed as an individual's health issue, it places a large burden on the health care system of a society. Individuals who are obese are at an increased risk for many serious diseases and health conditions. Some of these diseases and conditions include high blood pressure (hypertension), high low-density lipid (LDL) cholesterol, Type 2 diabetes, coronary heart disease, stroke, gallbladder disease, osteoarthritis, sleep apnea and other breathing prob-lems, cancer (especially esophageal adenocarcinoma, gastric cancer, liver cancer, kidney cancer, multiple myeloma, men-ingioma, pancreatic cancer, colorectal cancer, breast cancer, ovarian cancer, and thyroid cancer), depression, anxiety and other mental disorders, pain, restricted mobility, and decreased quality of life. Obesity also results in a higher mortality rate from all causes of death. Obesity-related health care costs in the United States have been estimated to be $147 billion per year.

Obesity is a leading risk factor for developing Type 2 diabetes, increasing the risk of developing Type 2 diabetes by approximately 28 times that of persons having a normal weight. Approximately 34 million people in the U.S. (about 1 in 10), and approximately 400 million worldwide, have diabetes. Moreover, about 88 million people in the U.S. are pre-diabetic, which is a serious health condition in which blood sugar levels are higher than normal but not high enough to be diagnosed as diabetic. Thus, obesity, and the related medical conditions of diabetes and pre-diabetes represent a challenge to the health care system. Relieving the obesity epidemic would also reduce the number of diabetic individuals.

The β3-adrenergic receptor (β3-AR) has long been a therapeutic target to combat obesity and metabolic disorders (e.g., diabetes, insulin resistance, etc.). β3-AR is abundantly expressed in rodent white adipose tissue (WAT) and brown adipose tissue (BAT), where it mediates lipolysis and ther-mogenesis. Moreover, adipocytes in BAT have high levels of mitochondria, and these mitochondria have high levels of uncoupling protein 1 (UCP1), which uncouples cellular respiration from adenosine triphosphate (ATP) synthesis and dissipates the energy in the form of heat. It is known that β3-AR agonists activate thermogenesis in adipose tissue, stimulating lipid oxidation and glucose consumption to produce heat. Further, studies have shown that treatment of rodents with β3-AR agonists activated BAT and beige fat (i.e., traditional white adipose tissue that takes on a pheno-type more similar to BAT, with increased mitochondrial density and greater glucose clearing ability), resulting in increased energy expenditure, weight loss, and improved glucose and lipid metabolism. Similarly, it has been shown that treatment of obese human individuals with the β3-AR agonist mirabegron reduced white adipose tissue dysfunc-tion.

While β3-AR agonists show promise for treating obesity, they do cause unwelcome side effects. For example, admin-istration of mirabegron may result in hypertension, nasoph-aryngitis, tachycardia, headaches, urinary tract infections, upper respiratory tract infections, constipation, abdominal pain, and fatigue. Moreover, mirabegron is contraindicated in people with liver or kidney problems, high blood pres-sure, or who have QT prolongation.

Thus, there is still a need for therapeutic compounds that can be used to treat obesity, and related diseases such as diabetes and pre-diabetes, either alone or in combination with other therapies. The present application addresses this need and provides other benefits as well.

SUMMARY

The disclosure relates to a method of treating obesity, treating diabetes, and treating obese breast cancer, by increasing the activity of uncoupling protein 1 (UCP1) in adipocytes, thereby increasing mitochondrial metabolism. Increasing the activity of UCP1 is achieved by contacting an adrenergic receptor agonist with an adipocyte in which the genomic activity of estrogen receptor beta (ERβ) has been inhibited or inactivated. In certain aspects, inhibition or inactivation of the genomic activity of ERβ is achieved by contacting the adipocyte with an ERβ ligand that selectively inhibits or inactivates the ERβ genomic activity. In some forms, the inhibition or inactivation of the Erβ genomic activity is achieved by antagonizing or eliminating ERβ nuclear genomic activity. In some forms, the inhibition or inactivation of the Erβ genomic activity is achieved by enhancing the protein-protein interaction domain of ERβ. In some forms, the increased activation of this non-DNA binding domain of the receptor allows for mitochondrial translocation and the subsequent increase in mitochondrial OX PHOS activity.

One embodiment is a method of increasing or enhancing transcription of uncoupling protein 1 (UCP1) in an adipo-cyte, comprising contacting the adipocyte with a beta 3 adrenergic receptor (β3AR) agonist and an estrogen receptor beta (ERβ) ligand, wherein the ERβ ligand selectively antagonizes the genomic effects of ERβ.

One embodiment is a method of enhancing the effective-ness of a beta 3 adrenergic receptor (β3AR) agonist in an adipocyte, comprising contacting the adipocyte with an estrogen receptor beta (ERβ) ligand, wherein the ERβ ligand selectively antagonizes the genomic effects of ERβ.

One embodiment is a method of increasing the metabo-lism of an adipocyte, comprising contacting the fat cell with a beta 3 adrenergic receptor (β3AR) agonist and an estrogen receptor beta (ERβ) ligand, wherein the ERβ ligand selec-tively antagonizes the genomic effects of ERβ.

In these embodiments, the adipocyte may be in vitro. In these embodiments, the adipocyte may be in vivo.

One embodiment is a method of enhancing the effectiveness of a beta 3 adrenergic receptor (β3AR) agonist in an individual receiving the β3AR agonist, comprising administering to the individual an estrogen receptor beta (ERβ) ligand, wherein the ERβ ligand selectively antagonizes the genomic effects of ERβ. In certain aspects, the individual may be receiving the β3AR agonist to treat obesity, glucose intolerance, pre-diabetes, diabetes, or obese breast cancer.

One embodiment is a method of increasing lipolysis in an individual, comprising administering to the individual a beta 3 adrenergic receptor (β3AR) agonist and an estrogen receptor beta (ERβ) ligand, wherein the ERβ ligand selectively antagonizes the genomic effects of ERβ.

One embodiment is a method of inducing or enhancing fat loss in an individual, comprising administering to the individual a beta 3 adrenergic receptor (β3AR) agonist and an estrogen receptor beta (ERβ) ligand, wherein the ERβ ligand selectively antagonizes the genomic effects of ERβ.

One embodiment is a method of treating obesity in an individual, comprising administering to the individual a beta 3 adrenergic receptor (β3AR) agonist and an estrogen receptor beta (ERβ) ligand, wherein the ERβ ligand selectively antagonizes the genomic effects of ERβ.

One embodiment is a method of increasing glucose tolerance in an individual, comprising administering to the individual a beta 3 adrenergic receptor (β3AR) agonist and an estrogen receptor beta (ERβ) ligand, wherein the ERβ ligand selectively antagonizes the genomic effects of ERβ.

One embodiment is a method of treating diabetes in an individual, comprising administering to the individual a beta 3 adrenergic receptor (β3AR) agonist and an estrogen receptor beta (ERβ) ligand, wherein the ERβ ligand selectively antagonizes the genomic effects of ERβ. In these embodiments, the ERβ ligand may cause increased localization of ERβ to mitochondria. In these embodiments, the β3AR agonist may bind to β3AR.

One embodiment is a method of treating obese breast cancer, comprising administering to the individual a beta 3 adrenergic receptor (β3AR) agonist and an estrogen receptor beta (ERβ) ligand, wherein the ERβ ligand selectively antagonizes the genomic effects of ERβ. In one aspect, administration of β3AR may reduce invasiveness of cancer cells. In these embodiments, the ERβ ligand may cause increased localization of ERβ to mitochondria. In these embodiments, the β3AR agonist may bind to β3AR.

One embodiment is a therapeutic composition comprising a beta 3 adrenergic receptor (β3AR) agonist and an estrogen receptor beta (ERβ) ligand, wherein the ERβ ligand selectively antagonizes the genomic effects of ERβ.

One embodiment is a kit comprising a beta 3 adrenergic receptor (β3AR) agonist and an estrogen receptor beta (ERβ) ligand, wherein the ERβ ligand selectively antagonizes the genomic effects of ERβ. In these embodiments, the ERβ ligand may cause increased localization of ERβ to mitochondria. In certain aspects, the kit may comprise additional components, such as vials, buffers, needles, syringes, and instructions for using the contents of the kit according to a method disclosed herein.

In these embodiments, the ERβ ligand may cause increased localization of ERβ to mitochondria. In these embodiments, the ERβ ligand may selectively antagonize the genomic effects of ERβ. In these embodiments, the ERβ ligand may comprise LY3201, s-equol, LY500307, or PHTPP. In these embodiments the β3AR agonist may comprise Mirabegron, CL316,243, or BRL37344.

BRIEF DESCRIPTION OF THE DRAWINGS

FIG. 1A shows a Western blot of proteins from inguinal subcutaneous adipose tissue using antibodies for ERβ, UCP1, and β-actin (internal control). The levels of ERβ and UCP1 proteins in wild-type (WT) and estrogen receptor beta (ERβ) DNA-binding domain (DBD) knock-out (ERβDBDKO), diet-induced obese mice that were either untreated, or given daily injections of CL316,243 (CL) are provided.

FIG. 1B is a graph comparing the intensity of the ERβ bands in FIG. 1A. The levels of ERβ and UCP1 proteins in wild-type (WT) and estrogen receptor beta (ERβ) DNA-binding domain (DBD) knock-out (ERβDBDKO), diet-induced obese mice that were either untreated, or given daily injections of CL316,243 (CL) are provided.

FIG. 1C is a graph comparing the intensity of the UCP-1 bands in FIG. 1A. The levels of ERβ and UCP1 proteins in wild-type (WT) and estrogen receptor beta (ERβ) DNA-binding domain (DBD) knock-out (ERβDBDKO), diet-induced obese mice that were either untreated, or given daily injections of CL316,243 (CL) are provided.

DETAILED DESCRIPTION

Figures 2A, 2B:
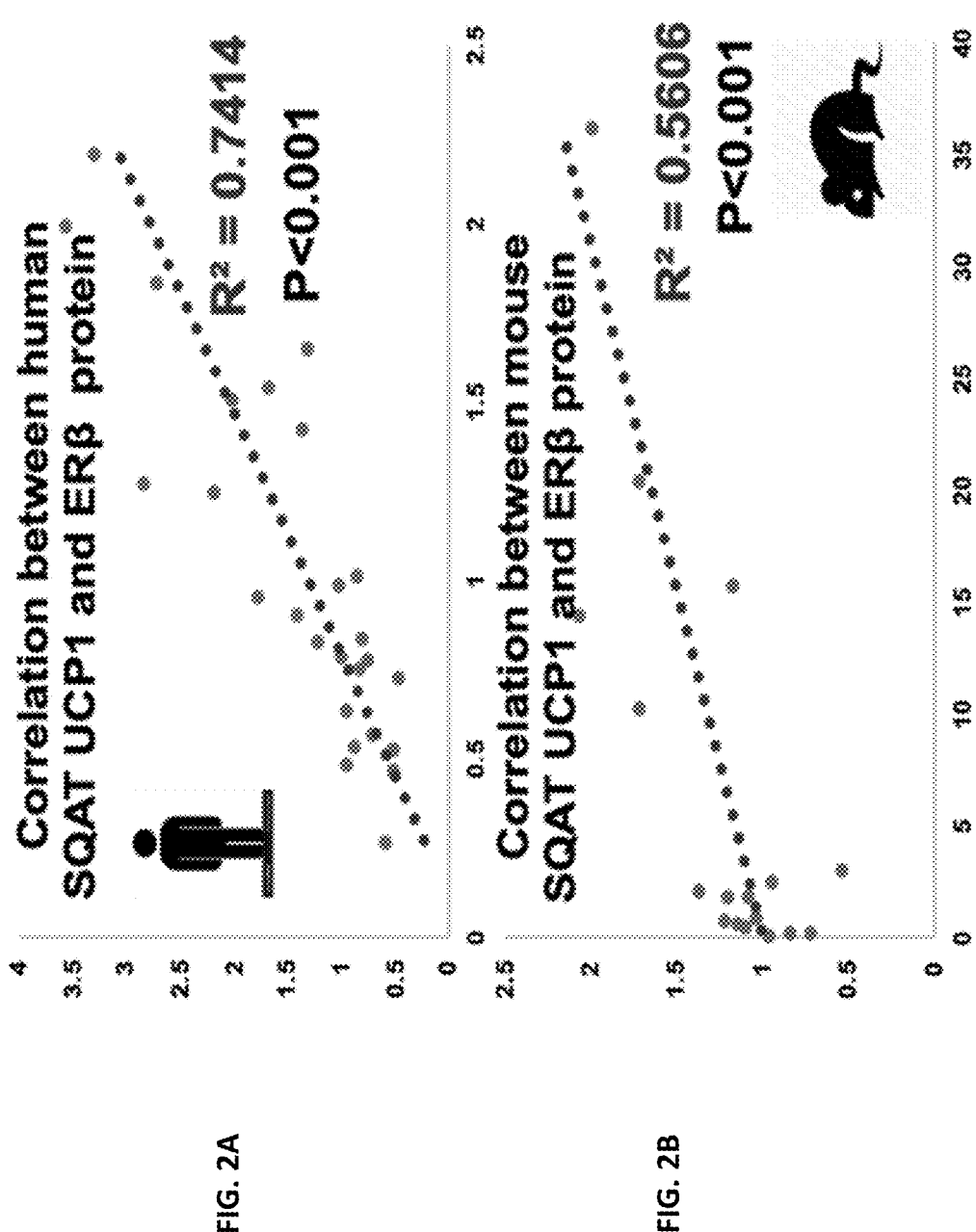
FIG. 2A illustrates the correlation between UCP1 and ERβ in WAT of humans.
FIG. 2B illustrates the correlation between UCP1 and ERβ in WAT of mice.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The present disclosure is related to methods of treating obesity and pre-diabetes. More specifically, the disclosure is based on the inventor's discovery of the relationship between estrogen receptor beta (ERβ) and uncoupling protein 1 (UCP1). The inventors have discovered that the two proteins interact to affect mitochondrial metabolism in adipose tissue. In particular, the inventors have discovered that ERβ is necessary for expression of UCP1. Additionally, the inventors have discovered that inhibition of the genomic activity (i.e., transcription activation or suppression) of ERβ renders the UCP1 protein more sensitive to induction by adrenergic receptor (AR) agonists, such as CL316243. Further, the inventors discovered that inhibition of the genomic activity of ERβ causes upregulation of the β3AR on adipocytes, supporting a potential mechanism for the heightened sensitivity to the β3AR agonists in this setting. Thus, modulation of ERβ activity may be used to affect the activity of UCP1, thereby affecting mitochondrial metabolism. Accordingly, a method of the disclosure may generally be practiced by contacting an adipocyte in which the genomic activity of ERβ has been inhibited or inactivated, with a β3 adrenergic receptor agonist. In certain aspects, inhibition or inactivation of ERβ genomic activity may comprise contacting the adipocyte with an ERβ ligand. In certain aspects, the adipocyte may be in vivo.

One embodiment comprises a method comprising contacting an adipocyte in which the genomic activity of ERβ has been inhibited or inactivated, with a β3 adrenergic receptor (β3AR) agonist. The method may comprise inhibiting or inactivating the genomic activity of genomic activity of ERβ by contacting the adipocyte with an ERβ ligand that selectively inhibits or inactivates the genomic activity of ERβ. In certain aspects, the adipocyte is in white adipose tissue (WAT). In certain aspects, the adipocyte is in brown adipose tissue (BAT). In certain aspects, the adipocyte is in beige adipose tissue.

Genomic activity of ERβ refers to regulation of gene expression by ERβ. Such regulation may comprise activation of enhancement of gene expression and/or suppression of gene expression.

Inhibition or inactivation or genomic activity refers to a decrease in, or complete elimination of, ERβ-mediated regulation of at least one gene. Inhibition or inactivation of ERβ genomic activity may result in a decrease, or elimination, of gene transcription, or it may result in an increase in transcription of a gene.

An adrenergic receptor agonist is any compound that stimulates a response from β3AR, resulting in an increase in UCP1. Examples of suitable β3AR agonists include, but are not limited to Mirabegron, CL316,243, or BRL37344.

An ERβ ligand refers to any compound that selectively inhibits or inactivates the genomic activity of ERβ. Examples of suitable ERβ ligands include, but are not limited to, LY3201, s-equol, LY500307, and 4-[2-phenyl-5, 7-bis(trifluoromethyl)pyrazolo[1,5-a]pyrimidin-3-yl]phenol (PHTPP).

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1. Effect of the β3-AR Agonist CL316243 on UCP1 and ERβ Protein Levels

Inguinal subcutaneous adipose tissue was harvested from diet-induced obese male and female wild-type (WT) and estrogen receptor beta (ERβ) DNA-binding domain (DBD) knock-out (ERβDBDKO) mice that were given daily injections of CL316,243 (CL), a beta3 adrenergic receptor (B3AR) ligand, for two weeks. ERβDBDKO mice express a mutated form of ERβ that lacks genomic activity by genetic ablation of the DBD, however still retain non-classical (i.e., non-genomic) signaling through ERβ. Protein was then isolated from the adipose tissue using Thermo Scientific™ RIPA lysis and extraction buffer, quantified using BCA method, then 10 ug was separated on a 4-20% SDS-PAGE gel followed by transfer to polyvinylidene difluoride membranes using BioRad Trans-Turbo Blot system. Blots were blocked in nonfat dry milk and western blotting was performed for ERβ (abcam, ab3576), the mitochondrial uncoupling protein 1 (UCP1) (Abcam, ab10983) and beta actin (abcam, ab8227). SuperSignal west femto chemiluminescent substrate (Thermo Scientific, #34096) was used to develop images after incubation in anti-rabbit IgG linked horseradish peroxidase antibody (Cell Signaling, #7074). Images were captured on a ChemiDoc Imaging System (BioRad, Hercules, CA), band intensity was quantified using ImageLab software (BioRad), then ERβ and UCP1 protein expression was quantified relative to beta actin. The results are shown in FIGS. 1A-1C.

FIG. 1A is a Western blot showing the levels of ERβ and UPC1 in WT and ERβDBDKO ("KO") mice, in the presence and absence of CL316243 ("CL"). The blot in FIG. 1A was scanned to quantify the band intensity, and the data used to graph the relative protein fold change for ERβ (FIG. 1B) and UCP-1 (FIG. 1C).

The data demonstrates that CL increases ERβ protein content in WAT to a greater level in ERβDBDKO mice compared to WT (FIG. 1B) (GxT, p<0.001). In addition, CL increases UCP1 protein content in ERβDBDKO mice more so than in WT mice (GxT, p=0.017) (FIG. 1C). N=9 per group; p<0.05 was considered statistically significant; statistics performed using SPSS V25.0. These data demonstrate for the first time in vivo that:

(1) ERβ genomic activity is not required for the CL-mediated induction of UCP1;

(2) knocking out the DBD of ERβ leads to pronounced ERβ expression in response to CL; and, (3) disrupting genomic activity of ERβ (i.e., promoting non-genomic ERβ functions) sensitizes WAT to CL-mediated UCP1 protein induction. Collectively these data support that ERβ directly affects adipocyte mitochondrial activity through novel non-genomic pathways. This is in agreement with previous observations by the inventors that there is a strong correlation between UCP1 and ERβ protein in WAT from both humans and rodents (FIG. 2).

Example 2. Requirement of ERβ for UCP1 Protein Expression in Primary Adipocytes from WAT To further explore the relationship between ERβ and UCP1, the levels of each protein were measured in primary adipocytes harvested from Esr-flox mice treated with Cre-

Figure 3C:
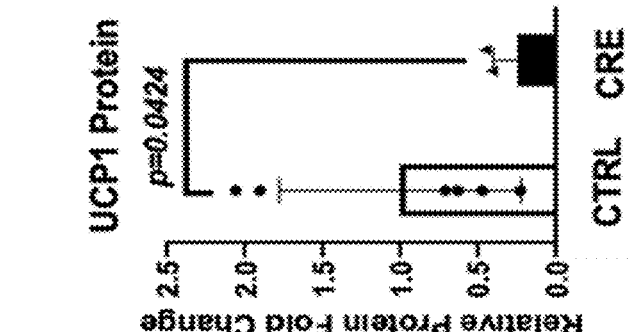
FIG. 3C is a graph comparing the intensity of the UCP-1 bands in FIG. 3A.
Figure 3B:
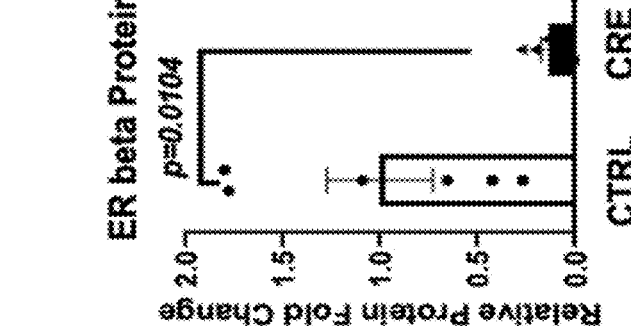
FIG. 3B is a graph comparing the intensity of the ERβ bands in FIG. 3A.
Figure 3A:
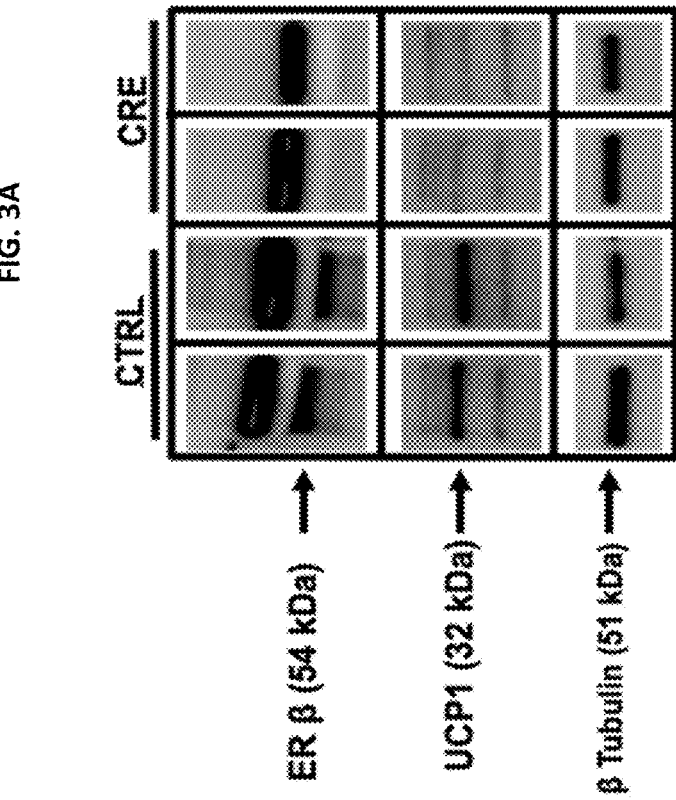
FIG. 3A shows a Western blot of proteins from perigonadal and inguinal subcutaneous adipose tissue using antibodies for ERβ, UCP1, and β-actin. The levels of ERβ protein and UCP1 protein in primary adipocytes harvested from Esr2-flox mice (Esr2 is the gene encoding ERβ; when exposed to Cre-recombinase, tissues from Esr2-flox mice should demonstrate significant knock-down of Erβ at the gene and protein level) are provided. The figure shows protein expression in adipocytes harvested from Esr2-flox mice that were either untreated (CTRL) or treated with Cre-recombinase (CRE).

7 recombinase. Briefly, perigonadal and inguinal adipose tissue (~3 grams) was harvested from one male Esr2-loxP floxed mouse$^{cre+/-}$ and digested in 1 mg/ml collagenase. Stromal vascular cells were then grown in Dulbecco's modified eagle medium/nutrient mixture F12 media supplemented with 10% fetal bovine serum, 1% GlutaMax, 0.1% gentamicin and 0.05% insulin at 37° C. and 5% $CO_2$. Adipocyte differentiation was induced by supplementing media with 0.5 mM 3-isobutyl-1-methylxanithon, 1 uM dexamethasone, and 1 mM rosiglitazone for 48 hours. Primary adipocytes were transfected 14 days after induction with $1.0 \times 10^8$ plaque-forming units/ml media recombinant adenovirus (Vector Biolabs, Malvern, PA) containing Cre recombinase (CRE), or eGFP (CTRL), under the CMV promoter, for 24 hours to attenuate expression of estrogen receptor beta (ERβ) (encoded by esr2). Protein was then isolated using Thermo Scientific RIPA lysis and extraction buffer and quantified using BCA method. 10 ug protein was separated on a 4-20% SDS-PAGE gel followed by transfer to polyvinylidene difluoride membranes using BioRad Trans-Turbo Blot system, blocked in nonfat dry milk then western blotting was performed for ERβ (abcam, ab3576), the mitochondrial uncoupling protein 1 (UCP1) (Abcam, ab10983) and beta tubulin (abcam, ab6046). SuperSignal west femto chemiluminescent substrate (Thermo Scientific, #34096) was used to develop images after incubation in anti-rabbit IgG linked horseradish peroxidase antibody (Cell Signaling, #7074). Images were captured on a ChemiDoc Imaging System (BioRad, Hercules, CA) and band intensity was quantified using ImageLab software (BioRad). ERβ and UCP1 protein expression were quantified relative to beta tubulin. The results of this study are shown in FIGS. 3A-C. The results demonstrate that knockdown of the complete ERβ protein suppresses UCP1 protein expression. (p=0.0424, t-test). N=6 per group; p<0.05 was considered statistically significant; statistics performed using GraphPad Prism9. Thus, ERβ is required for expression of UCP1 protein.

Example 3. Effect of Inhibiting Genomic Activity of ERβ on CL316243-Induced UCP1 Expression To test the hypothesis in vitro, that inhibition of genomic activity of ERβ would enhance the effectiveness of the PAR agonist, CL316,243 (CL) to induce expression of the mitochondrial UCP1, primary adipocytes were treated with the following: (a) CL, (b) diarylpropionitrile (DPN) (i.e., ligand known to promote classical genomic functions of ERβ), (c) 4-(2-phenyl-5,7-bis(trifluoromethyl)pyrazolo[1,5-a]pyrimidin-3-yl)phenol (PHTPP) (i.e., ligand known to suppress classical genomic functions of ERβ), (d) CL+DPN, and (e)

8

Figure 4:
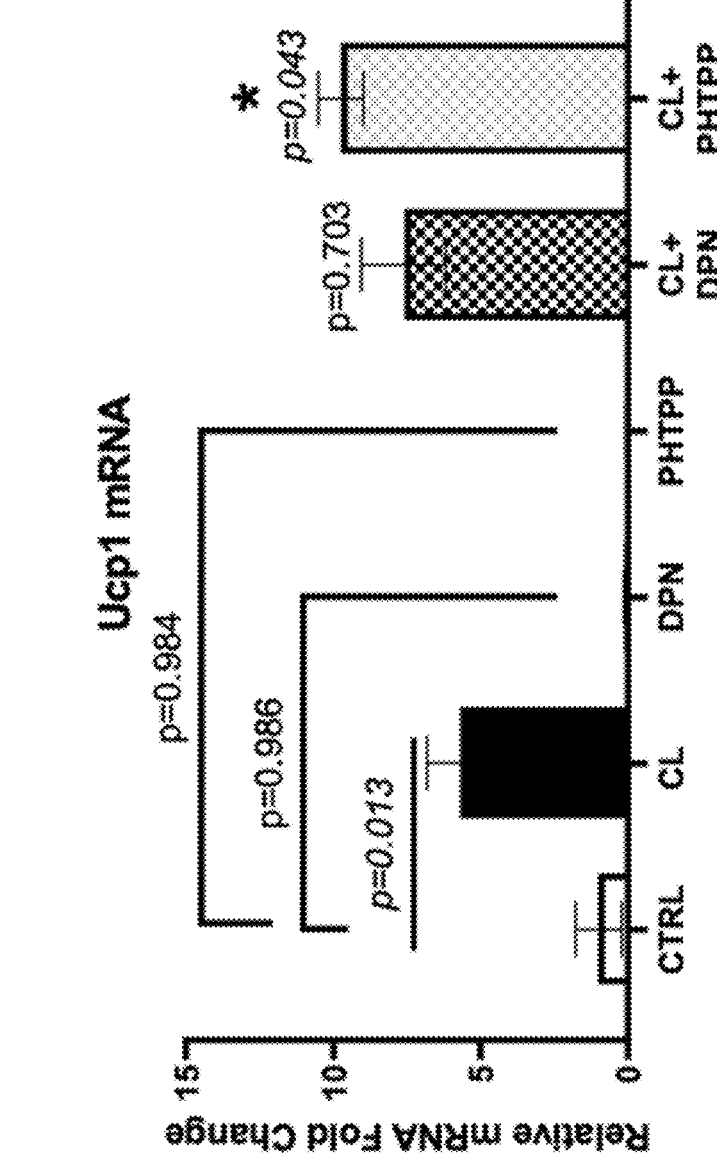
FIG. 4 shows the relative levels of UCP1 mRNA in primary adipocytes from mice, either untreated (CTRL), or treated with CL, diarylpropionitrile (DPN), 4-(2-phenyl-5, 7-bis(trifluoromethyl)pyrazolo[1,5-a]pyrimidin-3-yl)phenol (PHTPP), CL+DPN, and CL+PHTPP.

CL+PHTPP. Briefly, perigonadal and subcutaneous WAT was harvested from male C57BL6J mice, digested in collagenase to isolate stromal vascular cells then cultured in Dulbecco's modified eagle medium/nutrient mixture F12 media supplemented with 10% fetal bovine serum, 1% GlutaMax, 0.1% gentamicin and 0.05% insulin at 37° C. and 5% $CO_2$. Adipocyte differentiation was induced by supplementing media with 0.5 mM 3-isobutyl-1-methylxanithon, 1 uM dexamethasone, and 1 mM rosiglitazone for 48 hours. 14 days post induction, primary adipocytes were treated with either 1 uM CL, 10 nM DPN, 1 uM PHTPP or a combination of ligands as outlined above. After 24 hours treatment, ucp1 mRNA induction was measured using qRT-PCR. Beta-actin was used as a housekeeping gene as cycle thresholds (CT) was not different between groups. Ucp1 mRNA expression is expressed as $2^{\Delta CT}$ where ΔCT=housekeeping CT−Ucp1 CT and presented as fold difference relative to control (CTRL). N=8 per group; p<0.05 was considered statistically significant; statistics performed using SPSS V25.0. P-values comparing CL, DPN and PHTTP to CTRL are shown above lines in the figure, whereas p-values comparing CL+DPN and CL+PHTPP to CL alone are shown above respective bars. *Significant compared to CL alone. The results of this study are shown in FIG. 4.

These data demonstrate for the first time in vitro, that ERβ specific ligands influence the response to CL. Furthermore, these data support that inhibition of classical genomic activity of ERβ (e.g., via PHTPP) increases the CL-mediated induction of UCP1, suggesting that promoting novel nongenomic ERβ activity in adipocytes enhances mitochondrial activity through modulation of UCP1.

What is claimed is:

1. A method of increasing lipolysis, inducing fat loss, enhancing fat loss, treating obesity, decreasing adipocyte proliferation, decreasing glucose intolerance, or treating diabetes in an individual in need thereof, comprising the step of administering a beta 3 adrenergic receptor (β3AR) agonist and an estrogen receptor beta (ERβ) ligand to an individual in need thereof, wherein the ERβ ligand selectively antagonizes the genomic effects of ERβ.

2. The method of claim 1, wherein the ERβ ligand is selected to be one that causes increased localization of ERβ in mitochondria.

3. The method of claim 1, wherein the β3AR agonist binds to β3AR.

4. The method of claim 1, wherein the β3AR agonist comprises Mirabegron, CL316,243, or BRL37344.

5. The method of claim 1, wherein the ERB ligand comprises LY3201, s-equol, LY500307, or PHTPP.

* * * * *